United States Patent [19]

Simpson et al.

[11] 4,014,611
[45] Mar. 29, 1977

[54] APERTURE MODULE FOR USE IN PARTICLE TESTING APPARATUS

[75] Inventors: Ronald O. Simpson, Miami; Thomas J. Godin, West Hollywood, both of Fla.

[73] Assignee: Coulter Electronics, Inc., Hialeah, Fla.

[22] Filed: Apr. 30, 1975

[21] Appl. No.: 573,265

[52] U.S. Cl. .............................. 356/72; 324/71 CP
[51] Int. Cl.² .................. G01N 21/00; G01N 27/00
[58] Field of Search ............ 324/71 CP; 73/432 PS; 356/102, 72

[56] References Cited

UNITED STATES PATENTS

| | | | |
|---|---|---|---|
| 3,746,976 | 7/1973 | Hogg | 324/71 CP |
| 3,810,010 | 5/1974 | Thom | 324/71 CP |
| 3,902,115 | 8/1975 | Hogg et al. | 324/71 CP |

*Primary Examiner*—Vincent P. McGraw
*Attorney, Agent, or Firm*—Silverman & Cass, Ltd.

[57] ABSTRACT

An aperture module for obtaining signals from microscopic particles suspended in a fluid which passes through a scanning aperture. A module housing including an aperture holder is mounted on a vessel or bath containing a body of the particulate liquid suspension to be tested. The aperture holder with aperture formed therein extends into the vessel to permit passage of the suspension through the aperture to an outlet chamber or passageway immediately behind the aperture. An inlet chamber or passageway in the module is connected to a source of clean electrolyte and in fluid communication with the outlet passageway. The outlet passageway is connected to a waste collecting container. A vacuum is applied to the collecting container to cause the clean electrolyte to be drawn through the inlet passageway and wash behind the aperture simultaneously with passage of the suspension through the aperture. A restriction in the path of flow of the clean electrolyte immediately behind the aperture causes the flow velocity thereof to increase behind the aperture and ensure that the zone behind the aperture continuously is washed or swept and that particles which have been tested or sensed are carried away from the aperture so that proper signals from the particles in the suspension are obtained.

In a modified form of the aperture module a nozzle member is positioned between the bath and the aperture to form a sheath flow of electrolyte surrounding the particulate suspension to carry the suspension directly into and through the aperture into the passageway behind the aperture.

16 Claims, 6 Drawing Figures

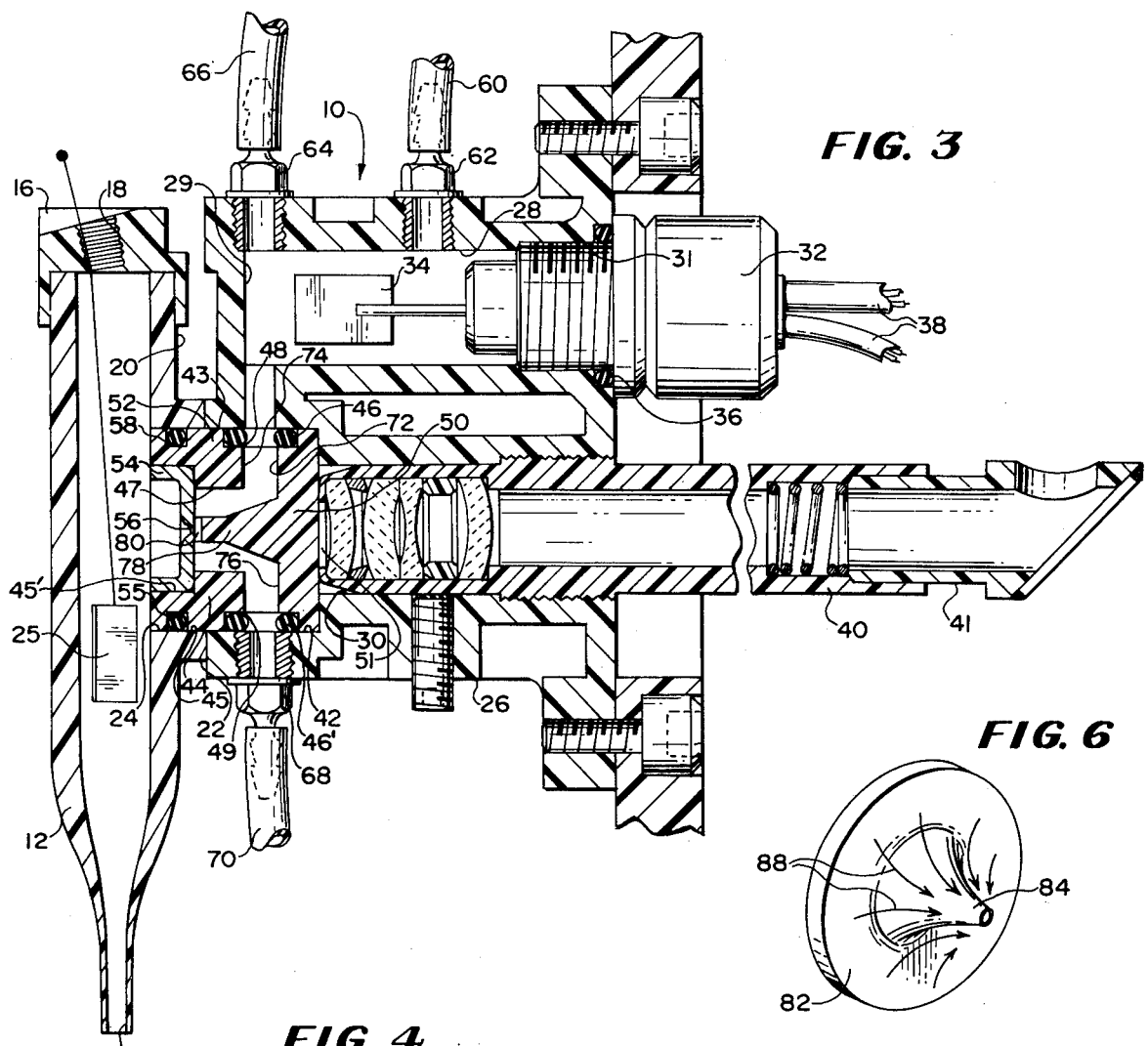
FIG. 3
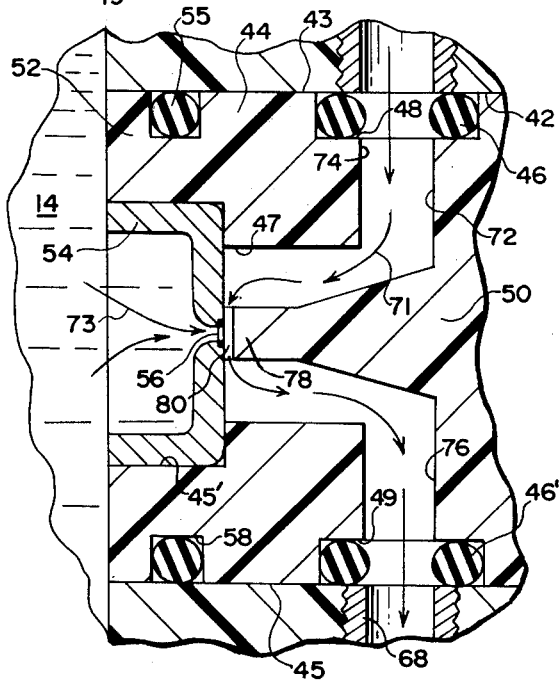
FIG. 4
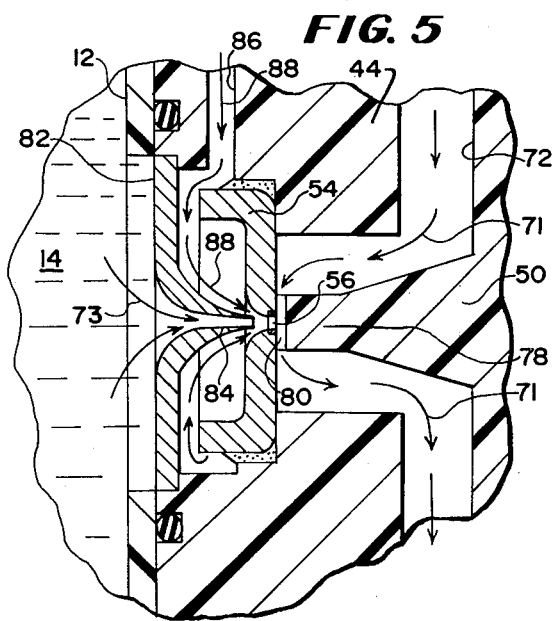
FIG. 5
FIG. 6

APERTURE MODULE FOR USE IN PARTICLE TESTING APPARATUS

CROSS REFERENCE TO RELATED APPLICATIONS

The structure to which this invention applies is of the type described and disclosed in U.S. application Ser. No. 400,986 filed Sept. 26, 1973, now U.S. Pat. No. 3,902,115 issued Aug. 26, 1975 (herein called "the Related Patent"), entitled "Self-Cleaning Aperture Tube for Coulter Study Apparatus and Electrolyte Supply System Therefore".

The present application also is related in part to the structures disclosed in U.S. Pat. Nos. 2,656,508, 3,299,354 and 3,567,321; for purposes of background and detailed description of certain elements referred to hereinafter, these three patents are incorporated herein as a part hereof by specific reference.

One further patent which is related to the subject of the present application is U.S. Pat. No. 3,746,976, now U.S. Pat. No. RE. 28,558 to which reference also will hereafter be made.

All of the above patents are owned by the same assignee as the present application.

BACKGROUND OF THE INVENTION

1. Field of the Invention

This invention relates generally to the art of studying the physical properties of microscopic particles carried in suspension and more particularly is concerned with improved structure for obtaining signals from particles passing through a scanning aperture mounted in a module without extraneous interference from other particles.

2. Description of the Prior Art

The Related Patent discusses a specific problem which occurred during use of the aperture tube disclosed in U.S. Pat. No. 3,299,354. The structure of U.S. Pat. No. 3,299,354 substantially decreased the possibility of undesirable spurious particle reading and count signals which sometimes occurred in prior art devices. The aperture tube was self-cleaning in that the suspension in the immediate vicinity of the aperture was kept relatively free of extraneous particles. Despite the self-cleaning aspect of the structure of U.S. Pat. No. 3,299,354, eddy currents of fluid in the aperture tube at the downstream end of the primary bore could occur, and these eddy currents swirled into the secondary bore immediately adjacent the primary bore. The structure of U.S. Pat. No. 3,746,976 (U.S. Pat. No. RE. 28,558) improved on the structure of U.S. Pat. No. 3,299,354 with the addition of a pump device interposed between the first and second chambers of the aperture tube to produce a closed system in which there are no inlets or outlets other than the primary bore in the first chamber. In the structure of the Related Patent, several specific alternate forms of aperture retaining members or tubes are disclosed in which the spurious signal producing zone of the aperture tube continuously is washed simultaneously with passage of the suspension through the aperture such that particles which have been measured within the aperture and thereafter passing out of the same immediately are swept out of the spurious signal producing zone by the particle free liquid and moved into the outlet chamber.

Specifically in connection with the disclosure of the Related Patent, one of the aperture retaining members described therein is a generally U-shaped tube with the aperture positioned in the side of one leg of the tube. A V-shaped restriction is formed in the wall of the U tube opposite the aperture to increase the flow velocity of electrolyte as it passes behind the aperture. Clean electrolyte flows down one leg of the tube and provides a continuous washing or sweep flow effect behind the aperture by reason of the restriction. The wash or sweep flow electrolyte together with the sample which has been drawn through the aperture then leaves the U tube through the exit leg. The spurious signal producing zone behind the aperture proximate the V-shaped restriction is continuously washed to maintain the same free of particles.

The basic concept of the referred-to structure of the Related Patent is satisfactory for accomplishing the object of continuously washing the spurious signal producing zone in the aperture retaining member but is relatively fragile and awkward for use in sophisticated commercial structures. The structure of the present application utilizes the concept of the Related Patent in a more practical module adapted specifically for use in presently developed sophisticated particle analyzing devices.

The technology represented by the pioneer U.S. Pat. No. 2,656,508 has burgeoned with world-wide utilization of the electronic particle studying apparatus disclosed therein. The vessel comprising a simple test tube with an aperture in its side walls shown in U.S. Pat. No. 2,656,508 was just that in commercial instruments made in the infancy of the art and many of the instruments of today still utilize this specific structure. The vessel has over the years become known as an "aperture tube". Added functions of improved versions of the well-known aperture tube have in many cases resulted in physical changes that render the same almost unrecognizable. In the structure of this application it has been deemed appropriate to refer to the aperture tube as being part of a "module" because of its relationship to other structure and ts many added functions as well as its departure from tubular appearance, but it should be kept in mind in the reading of this specification and claims that the primary and most basic function of the module is common to that of the classic aperture tube — hence, it is the equivalent thereof with respect to this basic function.

SUMMARY OF THE INVENTION

The invention provides an aperture module for use in a particle study apparatus of the type disclosed in the Related Patent. The module includes an aperture holder for mounting on a vessel or bath containing particulate sample solution to be tested. The aperture holder with aperture formed therein extends into the bath to permit passage of the suspension through the aperture to an outlet chamber or passageway immediately behind the aperture. An inlet chamber or passageway in the module is connected to a source of clean electrolyte and in fluid communication with the outlet passageway. A restriction is positioned in the passageways immediately behind the aperture. Clean electrolyte is passed through the passageways to wash or sweep behind the aperture where the flow velocity thereof is increased by reason of the restriction. Simultaneously with passage of clean electrolyte behind the aperture, the suspension in the bath is drawn through the aperture but immediately is carried away therefrom by the sweep flow electrolyte to ensure that particles which have been tested or sensed proximate the aperture do not remain to produce spurious signals.

In an alternate embodiment of the invention, a sheath flow nozzle is positioned in the aperture holder immediately upstream of the aperture to provide for sheath flow of clean electrolyte to surround the particle suspension just prior to entering the aperture and enhance passage of the suspension directly into the aperture thereafter to be washed away by the sweep flow electrolyte behind the aperture.

BRIEF DESCRIPTION OF THE DRAWINGS

FIG. 3 is a sectional view taken along the line 3—3 of FIG. 1 in the direction indicated generally;

FIG. 4 is an enlarged view of a portion of the module and bath shown in FIG. 3 which includes the aperture dish and sweep flow passageway;

FIG. 5 is a view similar to that of FIG. 4 illustrating an alternate form of the invention with the sheath flow nozzle thereof in position; and FIG. 6 is a perspective view of the sheath flow nozzle shown in FIG. 5.

DESCRIPTION OF THE PREFERRED EMBODIMENTS

The apparatus with which the aperture module of the invention is intended for use is known as the Coulter electronic particle analyzing device. (The mark "Coulter" is the Registered Trademark, Registration No. 995,825, of Coulter Electronics, Inc. of Hialeah, Florida). The Coulter device and its principle of operation is referred to with particularity in U.S. Pat. Nos. 2,656,508 and 3,299,354. Since these patents are incorporated herein as a part hereof by specific reference, the disclosures thereof will not be repeated except in instances where understanding of the invention herein will be enhanced.

Figure 1:
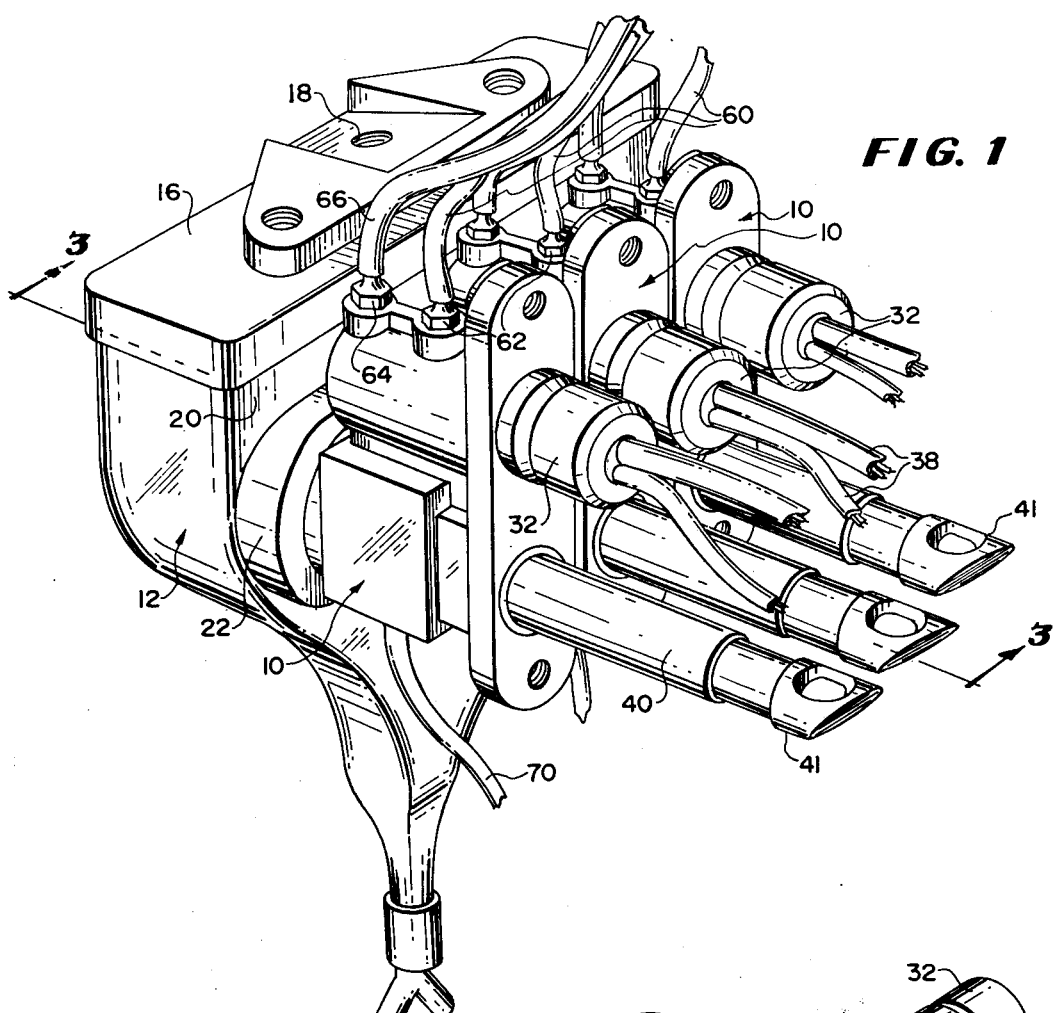
FIG. 1 is a perspective view of three aperture modules of the invention mounted on a bath containing the particulate suspension to be tested.

The aperture module of the invention is referred to generally by the reference numeral 10. In FIG. 1, three such modules 10 are shown mounted on a container or bath 12. The general construction of bath 12 is described in detail in U.S. Pat. No. 3,567,321 and reference is made thereto for a more complete description thereof. It is to be understood that while three aperture modules 10 are shown in FIG. 1 mounted on the bath, the structure of the present invention is totally independent of the number of modules which are so mounted in use.

The bath 12 retains a body of sample solution 14 to be tested. There is a cover plate 16 with a sample supply port 18 for filling the bath and there is a drain opening 19 connected to suitable conduits and valve members for selectively draining the bath when desired. One side wall 20 of the bath 12 has a plurality of annular bosses 22 formed integrally therewith, having coaxial passageways 24 communicating with the interior of the bath. In the embodiment shown, there are three such bosses 22 corresponding to the number of modules 10 mounted on the bath.

Figure 2:
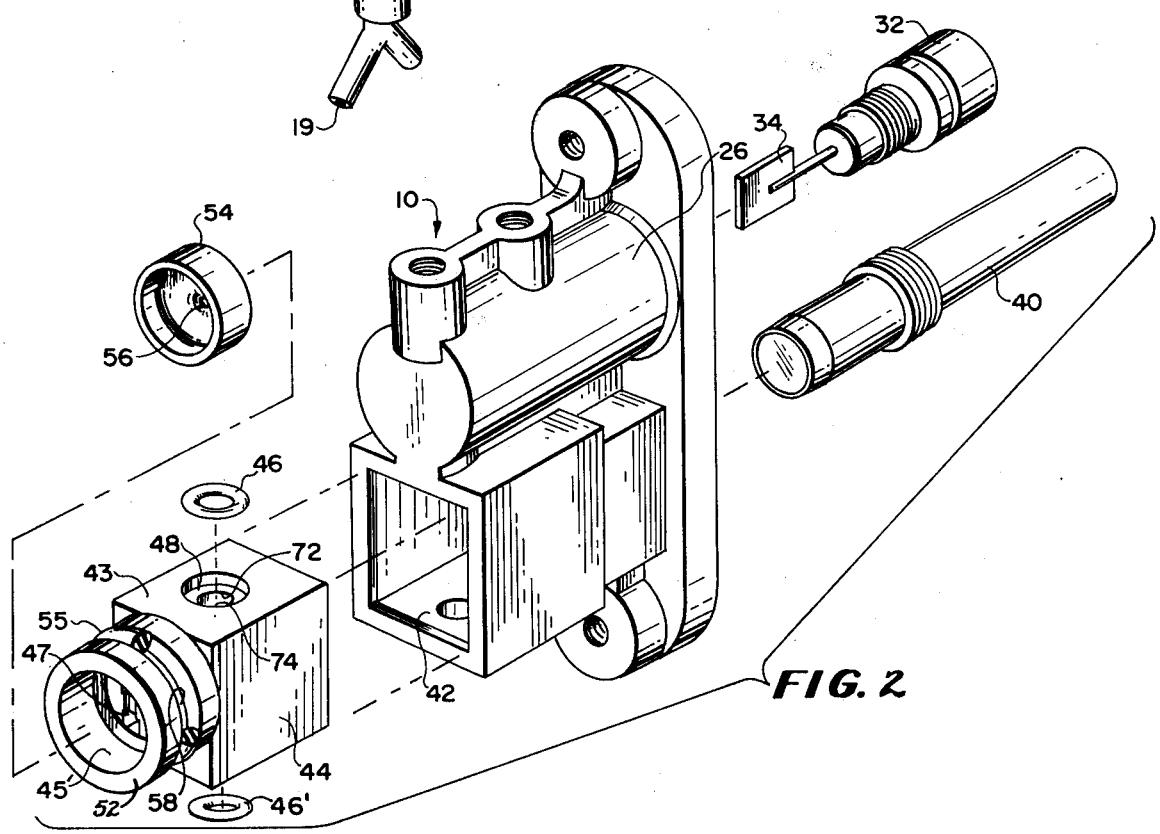
FIG. 2 is an exploded perspective view of one of the aperture modules shown in FIG. 1.

The aperture module 10 is comprised of a housing part 26 with two chambers 28, 39 formed therein. Chamber 28 has a blind end 29 and is adapted for receipt in open end 31 of an electrode cable assembly 32 which carries the signal electrode 34 for the Coulter device of which the module forms a part. (A ground electrode 25 is provided in bath 12 as required in such device). The assembly 32 is sealingly engaged in chamber 28 by any suitable means such as O-ring 36 to prevent escape of fluid from open end 31 of the chamber. Electric leads 38 couple electrode 34 with the detector of the Coulter device. Chamber 30 extends through housing 26 and is adapted for receipt of objective lens assembly 40 which is provided for visually examining the actual opening of the aperture wafer of the module while it is in use. The lens assembly 40 illustrated in FIGS. 1 and 3 includes a mirror assembly 41 for projection of an image on a screen; assembly 40 is shown in FIG. 2 as a microscope without the assembly 41. A generally rectangular socket 42 is provided as an extension of the chamber 30 when the housing 26 is molded but which will be occupied, and hence closed off, when the aperture holder 44 is engaged therein as explained. Aperture holder 44 is removably retained within the socket 42 of the housing 26 by O-rings 46', 46 which are respectively disposed in annular pockets 48, 49 provided on opposite sides 43, 45 of the holder. The O-rings 46', 46' engage the opposite inner facing surfaces of socket 42 when holder 44 is secured in socket 42 as described below.

It will thus be apparent that aperture holder 44 which carries the aperture of the Coulter device is completely removable from housing 26 as most clearly illustrated in FIG. 2. In the event it is required to change an aperture for whatever reason, holder 44 may conveniently and quickly be withdrawn from socket 42 and a fresh holder 44 with new aperture can be plugged-in socket 42 without the need for replacement of the entire module 10.

Aperture holder 44 is best seen in FIGS. 2 and 4. It is formed of a cube of transparent synthetic resin such as high impact polystyrene or other material which will not react with the reagents to which it will be exposed. It is required to transmit light with as little distortion as possible, as explained in U.S. Pat. No. 2,656,508. As noted, the holder 44 has a vertically arranged passageway 72 drilled or otherwise formed therein and a transverse passageway 47 formed normal to passageway 72. The vertically arranged passageway 72 opens on sides 43, 45 of the holder in the annular pockets 48, 49. The aperture holder 44 has an imperforate wall 50 which forms a blind end 51 for the chamber 30 when the holder is positioned within rectangular socket 42 as shown such that lens assembly 40 is disposed adjacent the closed end 51. The left hand part of the body of holder 44 has a cylindrical extension 52 carrying the cavity or inlet opening 45' coaxial with transverse passageway 47 in aperture holder 44. The cavity 45' is adapted for receipt of aperture dish 54 with aperture 56 formed therein in the manner described in the Related Patent, for example. Alternatively, aperture 56 may be formed in a disc or wafer (not shown), and the disc positioned in cavity 45'.

Aperture dish 54 is secured within cavity 45' by cement or other suitable means. Extension 52, as previously mentioned, has an external configuration corresponding generally to the opening 24 in boss 22 of bath 12 such that module 10 is mountable upon bath 12 by telescopically engaging extension 52 within opening 24. O-ring 55 is disposed within groove 58 upon extension 52 to seal the extension within the bath opening and prevent fluid leakage therefrom.

A source of clean electrolyte (not shown) is supplied to module 10 through conduit 60 connected over fitting 62 which opens to chamber 28. Another fitting 64 opens to chamber 28 and is connected by conduit 66 to a scavenge isolator (not shown) for flushing and purging the module of fluid which has been introduced thereto. A fitting 68 is threaded into the bottom wall of the socket part of the housing 26 with its passageway in alignment with and opening into the bottom pocket 49. When fitting 68 is in position as shown in FIG. 3, it abuts O-ring 46' to compress the same and thereby firmly retain holder 44 in socket 42. Fitting 68 opens to socket 42 of chamber 30 and is connected by conduit 70 to a collecting container or isolator (not shown) to which a vacuum source may be applied.

Passageway 72 in aperture holder 44 opens at one end 74 thereof to chamber 28 and at the other end 76 to fitting 68. The O-rings 46, 46' seal the juncture of passageway 72 at its open ends with chamber 28 and fitting 68 to provide liquid-tight connection therebetween. A diversion or projection 78 is formed in the passageway 72 on closed end 50 extends within the passageway to a location in close proximity to aperture 56 thereby forming a restriction 80 in the passageway 72. Clean electrolyte may be introduced to module 10 by drawing a vacuum through conduit 70 which will cause the electrolyte to enter chamber 28, pass therethrough into passageway 72 through entrance end 74 thereof, around the projection 78 and past restriction 80 and thereafter exit from the passageway 72 through fitting 68 and conduit 70 to the waste isolater. This flow of electrolyte is indicated in FIG. 4 by arrow 71.

Assuming that the aperture 56 is plugged, the suction applied to passageway 72 at end 76 will cause electrolyte to flow behind aperture 56; the flow velocity of electrolyte past restriction 80 is increased thereby creating a washing or sweep flow action behind the aperture. If the aperture is open as it will be in operation of the Coulter device, the sample 14 will be drawn into the aperture module 10 (arrows 73) at the same time that electrolyte is passing behind aperture 56. The clean electrolyte will sweep the sample coming through the aperture away from the zone surrounding restriction 80 and prevent particles from straying in the passageway 72, thus eliminating any swirling effect of undesirable eddy currents. The washing or sweep action created by the flow of electrolyte behind the aperture 56 is such as to ensure that all particles introduced into the aperture module are caught and carried away so as to prevent the occurrence of extraneous or spurious signals.

The restriction 80 behind the aperture 56 is such as to provide very high electrolyte flow rates without necessitating the use of large quantities of clean electrolyte. A criterion of performance satisfied by the aperture module 10 is that the speed of the sweep flow of clean electrolyte down past the aperture is greater than any upward components of any currents formed behind the aperture thus sweeping particles which have already been sensed out of the sensing zone in the area of the restriction 80 and preventing any particles from traveling upwards behind the aperture into the zone immediately upstream thereof where false pulses may be created.

FIGS. 5 and 6 illustrate a modified form of module 10 in which a nozzle member 82 is positioned between the bath 12 and the aperture dish 54 with the protruding nozzle portion 84 of member 82 terminating proximate aperture 56. An additional passageway 86 is provided in module 10 to carry clean electrolyte (arrows 88) down around the entrance of the aperture to pass therethrough into the area of restriction 80. The electrolyte 88 will form a generally tubular sheath flow around the nozzle while the suspension 14 is passing through the nozzle. The suspension thereby is surrounded by the electrolyte 88 immediately prior to entering the aperture 56 such that the sheath flow of the electrolyte 88 carries the suspension directly into the aperture. Thereafter, the suspenson is swept out of the restriction 80 by electrolyte 71 in the manner described theretofore.

Minor variations in the structure and other variations in the arrangement and size of the various parts may occur to those skilled in the art without departing from the spirit or circumventing the scope of the invention as set forth in the appended claims.

That it is desired to secure by Letters Patent of the United States is:

1. An aperture module for use in particle testing apparatus including a container of particulate liquid suspension to be tested, said module comprising, a housing having a first chamber and a second chamber, an aperture holder formed of optically clear material disposed in the second chamber and having an aperture provided therein, the aperture holder having a closed end and the closed end forming a wall in the second chamber, the aperture holder extending into the container with the aperture in communication on one side thereof with the liquid suspension, a passageway in the module connecting the chambers and passing through the aperture holder, the aperture being in communication on the side opposite said one side with the passageway, a first electrode in the container and a second electrode in the first chamber to establish an electrical field in the aperture between the container and the aperture module, there being a zone in the passageway proximate to the aperture in which spurious signals may normally be produced, means for connecting the passageway at an entrance thereof to a source of particle free liquid and means for connecting the pssageway at an exit thereof to fluid moving means to move the particle free liquid through the passageway and simultaneously move the suspension from the container through the aperture into the spurious signal producing zone, means including electrical leads connected to said electrodes and adapted to extend connections to a detector to respond to electrical measuring signals produced across said electrodes with passage of particles through said aperture, the aperture holder having a projection formed on the closed end of the aperture holder and extending into the passageway to form a restriction therein proximate the aperture to cause the flow velocity of the particle free liquid to increase in the spurious signal producing zone and continuously wash the zone simultaneously with passage of the suspension through the aperture such that particles which have passed through the aperture immediately are swept out of the spurious signal producing zone by the particle free liquid and moved to the exit of the passageway, and an objective lens assembly positioned in the second chamber adjacent said well formed by the closed end of the aperture holder on the side thereof opposite that having said projection for visually examining the aperture during movement of the suspension therethrough.

2. An aperture module as claimed in claim 1 in which the second chamber has a generally rectangular socket portion as an extension thereof and the aperture holder is disposed in the socket.

3. An aperture module as claimed in claim 1 in which the container is a bath having a side all with at least one circular boss forming an opening to the interior of the bath and the apertue holder has an extending part for telescopic mating engagement in the boss.

4. An aperture module as claimed in claim 3 in which an O-ring is positioned around the extending part and the holder is frictionally retained in the boss by the O-ring.

5. An aperture module as claimed in claim 3 in which the extending part of the aperture holder has a cylindrical cavity, an aperture dish retained in the cavity and the aperture being formed in the dish.

6. An apertue module as claimed in claim 1 in which the aperture holer is of generally cube-shaped configuration and has an imperforate wall blocking the second chamber.

7. An aperture module as claimed in claim 1 in which the passageway entrance opens to the first chamber.

8. An aperture module as claimed in claim 1 in which the module is formed of optically clear plastic.

9. An aperture module as claimed in claim 1 in which the aperture holer is removably retained within the second chamber.

10. An aperture module as claimed in claim 9 in which the holder is of generally cube-shaped configuration and has annular pockets on opposite sides thereof, a respective O-ring positioned within each pocket to engage opposite inner facing surfaces of the second chamber.

11. An aperture module as claimed in claim 10 including means to engage at least one O-ring and compress the same to maintain the holder within the second chamber.

12. An aperture module as claimed in claim 11 in which said means are a threaded fitting engaged against aid one O-ring.

13. An aperture module as claimed in claim 10 in which the passageway in the holder opens at either end thereof to the pockets.

14. An aperture module as claimed in claim 1 including a nozzle having a protruding portion, the nozzle being disposed between the container and the aperture with the protruding portion terminating proximate the aperture.

15. An aperture module as claimed in claim 14 in which the module includes a further passageway for supplying particle free liquid around the entrance of the aperture to pass therethrough with the liquid suspension.

16. An aperture module as claimed in claim 15 in which the liquid passing through the last named passageway forms a generally tubular sheath flow around the nozzle to surround the suspension and carry the same directly into the aperture.

* * * * *